United States Patent [19]

Buschken et al.

[11] Patent Number: 4,788,318

[45] Date of Patent: Nov. 29, 1988

[54] PROCESS FOR THE PRODUCTION OF 4,4,8,8,10-PENTAMETHYL-10-CYANO-BICYCLO[4.4.0]-DEC-1,6-EN-2-ONE

[75] Inventors: Wilfried Buschken, Haltern; Klaus Rindtorff, Recklinghausen, both of Fed. Rep. of Germany

[73] Assignee: Hüls Aktiengesellschaft, Marl, Fed. Rep. of Germany

[21] Appl. No.: 89,129

[22] Filed: Aug. 25, 1987

[30] Foreign Application Priority Data

Nov. 26, 1986 [DE] Fed. Rep. of Germany ....... 3640306

[51] Int. Cl.⁴ .......................................... C07C 120/02
[52] U.S. Cl. ..................................... 558/335; 558/341
[58] Field of Search ................................ 558/335, 341

[56] References Cited

U.S. PATENT DOCUMENTS

| | | | |
|---|---|---|---|
| 2,188,340 | 1/1940 | Dykstra | 558/341 |
| 3,337,423 | 8/1967 | Schmitt et al. | 568/353 X |
| 3,337,633 | 8/1967 | Schmitt et al. | 568/350 |
| 3,341,554 | 9/1967 | Murray et al. | 558/341 X |
| 4,299,775 | 11/1981 | Dubreux | 558/341 |

FOREIGN PATENT DOCUMENTS

| | | | |
|---|---|---|---|
| 632600 | 12/1961 | Canada | 558/341 |
| 685034 | 4/1964 | Canada | 558/341 |
| 887411 | 1/1962 | United Kingdom | 558/341 |
| 1047920 | 11/1966 | United Kingdom | 558/341 |

OTHER PUBLICATIONS

Noller, "Chemistry of Organic Compounds", 3rd ed., (1965), W. B. Saunders Co. (Philadelphia), p. 98.
Kirk-Othmer, "Encyclopedia of Chemical Technology", 3rd ed., vol. 13, (1981); pp. 918, 919, 920, 921, 922.

Primary Examiner—Joseph Paul Brust
Attorney, Agent, or Firm—Oblon, Fisher, Spivak, McClelland & Maier

[57] ABSTRACT

A process for the production of the bicyclic compound 4,4,8,8,10-pentamethyl-10-cyano-bicyclo[4.4.0]-dec-1,6-en-2-one which comprises the steps of (a) reacting a ketone fraction comprising

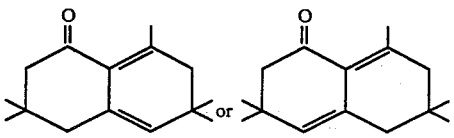

or mixtures thereof,
(b) by adding HCN to the ketone fraction the presence of a base, at a temperature of 50°–200° C. to obtain an addition product comprising the bicyclic compound, and
(c) isolating the addition product.

10 Claims, No Drawings

PROCESS FOR THE PRODUCTION OF 4,4,8,8,10-PENTAMETHYL-10-CYANO-BICYCLO[4.4.0]-DEC-1,6-EN-2-ONE

BACKGROUND OF THE INVENTION

1. Field of the Invention:

The invention relates to a process for the production of 4,4,8,8,10-pentamethyl-10-cyano-bicyclo[4.4.0]-dec-1,6-en-2-one [A] from a C15 ketone mixture, as it is obtained by fractionation of the sump product which occurs in the production of isophorone at 1 to 100 mbar with an approximately 30% yield, by the addition of hydrogen cyanide.

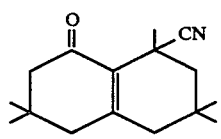

2. Discussion of Background:

Compound A is an excellent precursor for the synthesis of amines, diamines, heterocycles and a large number of other substances.

In the production of isophorone by the condensation of acetone, up to 10% condensation products with a higher molecular weight are formed, and at the present time, these are burned. Therefore, a need exists for processes to separate or convert this mixture into products which can be utilized synthetically.

The state of the art of isophorone production may be ascertained by reference to the Kirk-Othmer, Encyclopedia of Chemical Technology, 3rd Edition, Vol. 13 (1982), pages 918–922, particularly page 920 and U.S. Pat. Nos. 3,337,423 and 3,337,633, the disclosures of which are incorporated herein by reference.

SUMMARY OF THE INVENTION

Accordingly, one object of the present invention is to provide a method of producing 4,4,8,8,10-pentamethyl-10-cyano-bicyclo [4.4.0]-dec-1,6-en-2-one in an economical manner without using expensive reagents.

A further object of the invention is to provide a method of utilizing the sump product which occurs in the production of isophorone to produce useful chemical products.

These and other objects of the present invention which will become apparent from the following specification have been achieved by the present process for the production of the bicyclic compound 4,4,8,8,10-pentamethyl-10-cyano-bicyclo[4.4.0]-dec-1,6-en-2-one, comprising the steps of: producing a ketone fraction comprising

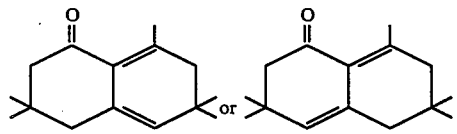

or mixtures thereof,
adding HCN to the ketone fraction in the presence of a base, at a temperature of 50°-200° C., to produce an addition product comprising said bicyclic compound, and isolating the addition product.

DETAILED DESCRIPTION OF THE PREFERRED EMBODIMENTS

Surprisingly, it was found that compound A can be obtained with a good yield and in excellent purity with process steps that are easy to carry out technically, by adding hydrogen cyanide to a special fraction of the isophorone sump product.

By fractionation of the isophorone sump product at 1 to 100 mbar, preferably at 10 to 30 mbar, a ketone fraction which consists essentially of C15 compounds is obtained. This ketone fraction, which is obtained with a yield of approximately 30%, boils at 125° to 145° C. at a pressure of 13 mbar. As the main components, this fraction contains the isomers B and C

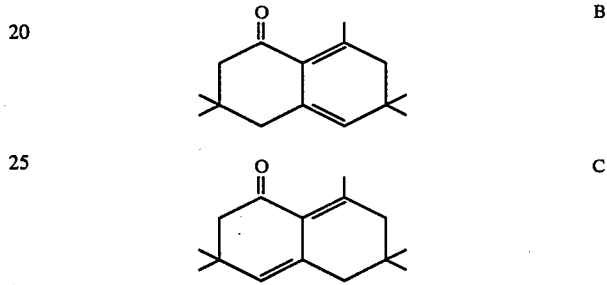

The position of the double bonds in B and C is not completely certain. Additionally, the ratio of the two isomers B and C to one another is not constant. Also, the content of both substances in the C15 fraction can differ. The total of both isomers in the C15 fraction is generally 75 to 90%.

The base-catalyzed addition of hydrogen cyanide to the C15 ketone fraction (Michael addition) surprisingly results in the same nitrile A from isomers B and C. It is furthermore surprising that hydrogen cyanide does not add to other compounds of the C15 ketone fraction and also that, no bis-HCN adduct with the structure D occurs.

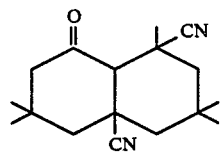

General basic substances are suitable as the basic catalyst. Preferably, alkali cyanides, alkali carbonates, alkali phenolates, alkali alcoholates, particularly the sodium salts are used, and the use of sodium methoxide is particularly preferred.

Base-catalyzed addition of hydrogen cyanide is carried out at temperatures from 50° to 200° C., preferably from 150° to 170° C.

Hydrogen cyanide is generally used in amounts of 5 to 10 wt. %, relative to the ketone fraction.

Instead of adding hydrogen cyanide to the C15 ketone sections with the isomers B and C obtained from the sump product of isophorone production, it can, of course be added to B and/or C which have been produced by any other suitable process.

The addition of hydrogen cyanide can be carried out continuously or batchwise. The addition can also be carried out in the presence of solvent.

The conversion mixture is diluted with light gasoline or a hydrocarbon such as hexane and distilled by fractionation after being washed with 1% acid, preferably nitric acid/water solution. Fractionation preferably takes place in a vacuum.

Other features of the invention will become apparent in the course of the following description of an exemplary embodiment which is given for illustration of the invention and is not intended to be limiting thereof.

EXAMPLE

The sump product of isophorone synthesis (by condensation of acetone) is fractionated at a pressure of 13 mbar. This results in a ketone fraction in a 30% yield (b.p. 125° to 145° C.), which consists essentially of C15 compounds, with the main components being compounds B and C.

100 g C15 ketone mixture (total B, C=89%) and 0.5 ml 30% methanolic NaOCH$_3$ solution were filled into a 1-liter stirring apparatus with a bottom valve, equipped with a dropping funnel and reflux condenser with a connected bubbler. At 170° C., a 30% methanolic NaOCH$_3$ solution was fed in through a metering pump, at a rate of 0.9 ml/h. At the same time, a solution of 420 g C15 ketone mixture (total B, C=89%) and 49.2 g HCN was dripped in. The HCN mixture was added as rapidly as the HCN reacted. With increasing reaction time, the conversion rate increased because of the increasing reaction volume. After 4.5 h, the entire solution had been added. The addition of catalyst was discontinued and the mixture was stirred at 170° C. for one hour. After it had cooled to 60° C., 350 ml hexane were added, and the mixture was washed once with 100 ml 1.5% nitric acid and once with 100 ml water. The n-hexane was drawn off and the residue (576 g) was distilled through a 60 cm packed column (b.p. 82° C.).

Obviously, numerous modifications and variations of the present invention are possible in light of the above teachings. It is therefore to be understood that within scope of the appended claims, the invention may be practiced otherwise than as specifically described herein.

reacting a ketone fraction comprising

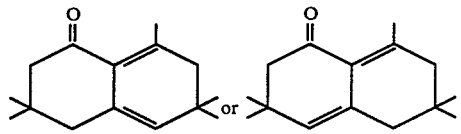

or mixtures thereof,
by adding HCN to said ketone fraction in the presence of a base, at a temperature of 150°-200° C. to obtain an addition product comprising said bicyclic compound, and
isolating said addition product.

2. The method of claim 1, wherein said isolating step comprises washing said addition product with aqueous acid and isolating said addition product by distillation.

3. The process of claim 1, wherein said base is selected from a group consisting of alkali cyanides, akali carbonates, alkali phenolates, alkali alcoholates and mixtures thereof.

4. The process of claim 3, wherein said base is selected from a group consisting of sodium cyanides, sodium carbonates, sodium phenolates, sodium alcoholates and mixtures thereof.

5. The process of claim 1, wherein said base is sodium methoxide.

6. The process of claim 1, wherein said adding step occurs at a temperature of from 150°-170° C.

7. The process of claim 1, wherein said ketone fraction comprises 75-90% of

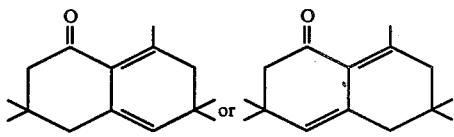

or mixtures thereof.

8. The process of claim 1, wherein said HCN is added in an amount of 5-10 wt. % relative to said ketone fraction.

9. The process of claim 1, wherein said ketone fraction is obtained by fractionating the sump product, which occurs during the production of isophorone by the condensation of acetone, at 1-100 mbar to produce said ketone fraction.

10. The process of claim 2, wherein said aqueous acid is aqueous nitric acid.

| | | Temperature °C. | | Pressure | Amount of Distillate | | Analytical Composition in % | | |
|---|---|---|---|---|---|---|---|---|---|
| Fraction | sump | mantle | head | (mbar) | (g) | % | ΣBC | ΣU | C$_{16}$—Nitrile A |
| 1 | 153-193 | 70-80 | 72-78 | 0.25 | 118.8 | 20.6 | 60 | 40 | 0 |
| 2 | 193-202 | 80-120 | 78-132 | 0.25 | 32.2 | 5.6 | 15 | 68.3 | 16.7 |
| 3 | 202-240 | 120-125 | 132-139 | 0.25-0.3 | 378.2 | 65.7 | — | — | 100 |
| 4 | (240-260) | 125-160 | 139-148 | 0.3 | 31.6 | 5.5 | — | 0.7 | 99.3 |
| residue | | | | | 2.6 | 0.5 | n.a. | n.a. | n.a. |
| cooling trap | | | | | 9.8 | 1.7 | n.a. | n.a. | n.a. |

Yield = 92% of theory calculated for HCN
79% of theory calculated for total B and C
U = unidentified products
n.a. — not applicable

What is claimed as new and desired to be secured by Letters Patent of the United States is:

1. A process for the production of the bicyclic compound 4,4,8,8,10-pentamethyl-10-cyanobicyclo[4.4.0]-dec-1,6-en-2-one, comprising the steps of: